(12) United States Patent
Gale et al.

(10) Patent No.: US 10,390,979 B2
(45) Date of Patent: Aug. 27, 2019

(54) MANUFACTURING PROCESS FOR POLYMERIC STENTS

(71) Applicant: Abbott Cardiovascular Systems Inc., Santa Clara, CA (US)

(72) Inventors: David C. Gale, Kennesaw, GA (US); Bin Huang, Pleasanton, CA (US); Anthony J. Abbate, Santa Clara, CA (US); Timothy A. Limon, Cupertino, CA (US); Klaus Kleine, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 20 days.

(21) Appl. No.: 15/379,665

(22) Filed: Dec. 15, 2016

(65) Prior Publication Data

US 2017/0095359 A1    Apr. 6, 2017

Related U.S. Application Data

(60) Division of application No. 14/255,896, filed on Apr. 17, 2014, now Pat. No. 9,554,925, which is a
(Continued)

(51) Int. Cl.
*A61F 2/915* (2013.01)
*B29C 48/09* (2019.01)
(Continued)

(52) U.S. Cl.
CPC ............... *A61F 2/915* (2013.01); *A61F 2/82* (2013.01); *A61F 2/91* (2013.01); *B23K 26/384* (2015.10); *B23K 26/402* (2013.01); *B29C 48/0022* (2019.02); *B29C 48/022* (2019.02); *B29C 48/09* (2019.02); *B29C 55/00* (2013.01); *B29C 65/02* (2013.01); *B29C 66/534* (2013.01); *B29C 71/0063* (2013.01); *A61F 2002/821* (2013.01); *A61F 2210/0004* (2013.01);
(Continued)

(58) Field of Classification Search
CPC ...... A61F 2/06; A61F 2/07; A61F 2/82; A61F 2/825; A61F 2/86; A61F 2/89; A61F 2/91; A61F 2/915; B29C 55/24
USPC ......... 29/508, 557, 558, 505, 515, 516, 446, 29/452; 623/1.15, 1.16; 219/121.6, 219/121.67, 121.69, 121.71, 121.72, 219/121.85
See application file for complete search history.

(56) References Cited

U.S. PATENT DOCUMENTS 3,636,956 A    1/1972    Schneider
4,547,416 A    10/1985   Reed et al.
(Continued)

FOREIGN PATENT DOCUMENTS

EP    0 583 170    2/1994
EP    1 800 628    6/2007
(Continued)

OTHER PUBLICATIONS

U.S. Appl. No. 10/956,910, filed Sep. 30, 2004, Huang et al.
(Continued)

*Primary Examiner* — Christopher M Koehler
(74) *Attorney, Agent, or Firm* — Squire Patton Boggs (US) LLP

(57) ABSTRACT

Methods and systems of fabricating a polymeric stent are disclosed herein.

7 Claims, 4 Drawing Sheets

Related U.S. Application Data continuation of application No. 14/252,689, filed on Apr. 14, 2014, now Pat. No. 9,198,782, which is a continuation of application No. 13/112,960, filed on May 20, 2011, now abandoned, which is a continuation of application No. 11/443,947, filed on May 30, 2006, now Pat. No. 7,971,333.

(51) Int. Cl.
| | | |
|---|---|---|
| *B29C 48/00* | (2019.01) | |
| *A61F 2/82* | (2013.01) | |
| *A61F 2/91* | (2013.01) | |
| *B29C 55/00* | (2006.01) | |
| *B29C 65/02* | (2006.01) | |
| *B29C 71/00* | (2006.01) | |
| *B23K 26/384* | (2014.01) | |
| *B23K 26/402* | (2014.01) | |
| *B29C 65/00* | (2006.01) | |
| *B23K 103/00* | (2006.01) | |
| *B29C 55/24* | (2006.01) | |
| *B29L 31/00* | (2006.01) | |

(52) U.S. Cl.
CPC ... *A61F 2210/0076* (2013.01); *B23K 2103/42* (2018.08); *B23K 2103/50* (2018.08); *B29C 55/24* (2013.01); *B29C 2793/0009* (2013.01); *B29K 2995/006* (2013.01); *B29K 2995/0039* (2013.01); *B29L 2031/7534* (2013.01); *Y10T 29/49874* (2015.01); *Y10T 29/49908* (2015.01); *Y10T 29/49913* (2015.01); *Y10T 29/49925* (2015.01); *Y10T 29/49927* (2015.01); *Y10T 29/49995* (2015.01)

(56) References Cited

U.S. PATENT DOCUMENTS

| | | | |
|---|---|---|---|
| 4,698,196 A | 10/1987 | Fabian et al. | |
| 4,702,884 A | 10/1987 | Goldstein | |
| 4,957,687 A | 9/1990 | Akman et al. | |
| 4,987,025 A | 1/1991 | Shiraki et al. | |
| 5,087,394 A | 2/1992 | Keith | |
| 5,108,416 A | 4/1992 | Ryan et al. | |
| 5,116,365 A | 5/1992 | Hillstead | |
| 5,147,302 A | 9/1992 | Euteneuer et al. | |
| 5,342,348 A | 8/1994 | Kaplan | |
| 5,500,013 A | 3/1996 | Buscemi et al. | |
| 5,514,154 A | 5/1996 | Lau et al. | |
| 5,591,230 A | 1/1997 | Horn et al. | |
| 5,628,786 A | 5/1997 | Banas et al. | |
| 5,670,161 A | 9/1997 | Healy et al. | |
| 5,741,327 A | 4/1998 | Frantzen | |
| 5,843,164 A | 12/1998 | Frantzen et al. | |
| 5,868,781 A * | 2/1999 | Killion | A61F 2/91 |
| | | | 606/198 |
| 5,868,782 A | 2/1999 | Frantzen | |
| 5,891,386 A | 4/1999 | Deitermann et al. | |
| 5,928,280 A | 7/1999 | Hansen et al. | |
| 6,042,606 A | 3/2000 | Frantzen | |
| 6,114,653 A * | 9/2000 | Gustafson | B23K 26/0823 |
| | | | 219/121.72 |
| 6,131,266 A * | 10/2000 | Saunders | A61F 2/91 |
| | | | 219/121.71 |
| 6,160,084 A * | 12/2000 | Langer | A61L 27/18 |
| | | | 528/176 |
| 6,206,911 B1 | 3/2001 | Milo | |
| 6,273,910 B1 | 8/2001 | Limon | |
| 6,312,459 B1 | 11/2001 | Huang et al. | |
| 6,327,772 B1 * | 12/2001 | Zadno-Azizi | A61F 2/88 |
| | | | 29/557 |
| 6,440,162 B1 * | 8/2002 | Cox | A61F 2/91 |
| | | | 623/1.15 |
| 6,500,146 B1 | 12/2002 | Pinchuk et al. | |
| 6,530,950 B1 | 3/2003 | Alvarado et al. | |
| 6,572,813 B1 | 6/2003 | Zhang et al. | |
| 6,612,012 B2 * | 9/2003 | Mitelberg | A61F 2/91 |
| | | | 148/426 |
| 6,616,689 B1 | 9/2003 | Ainsworth et al. | |
| 6,626,939 B1 | 9/2003 | Burnside et al. | |
| 6,629,994 B2 | 10/2003 | Gomez et al. | |
| 6,634,426 B2 | 10/2003 | McCoy et al. | |
| 6,638,300 B1 | 10/2003 | Frantzen | |
| 6,645,422 B2 | 11/2003 | Jung et al. | |
| 6,758,859 B1 | 7/2004 | Dang et al. | |
| 6,852,124 B2 | 2/2005 | Cox et al. | |
| 6,865,810 B2 * | 3/2005 | Stinson | A61F 2/91 |
| | | | 29/458 |
| 6,997,944 B2 | 2/2006 | Harrison et al. | |
| 6,997,946 B2 | 2/2006 | Girton et al. | |
| 7,066,952 B2 | 6/2006 | Igaki | |
| 7,070,615 B1 | 7/2006 | Igaki | |
| 7,083,639 B2 | 8/2006 | Guinan et al. | |
| 7,115,691 B2 | 10/2006 | Alvarado et al. | |
| 7,128,868 B2 | 10/2006 | Eidenschink | |
| 7,265,317 B2 * | 9/2007 | Koch | B23K 26/146 |
| | | | 219/121.71 |
| 7,273,492 B2 | 9/2007 | Cheng et al. | |
| 7,273,495 B2 | 9/2007 | Limon | |
| 7,291,166 B2 | 11/2007 | Cheng et al. | |
| 7,374,570 B2 | 5/2008 | Alvarado et al. | |
| 7,476,245 B2 | 1/2009 | Abbate | |
| 7,540,997 B2 * | 6/2009 | Stinson | A61L 27/047 |
| | | | 148/423 |
| 7,666,342 B2 | 2/2010 | Limon et al. | |
| 7,731,740 B2 | 6/2010 | LaFont et al. | |
| 7,731,890 B2 | 6/2010 | Gale et al. | |
| 7,761,968 B2 | 7/2010 | Huang et al. | |
| 7,763,066 B2 | 7/2010 | Parker | |
| 7,887,579 B2 | 2/2011 | Mangiardi et al. | |
| 7,971,333 B2 | 7/2011 | Gale et al. | |
| 8,002,817 B2 | 8/2011 | Limon | |
| 8,043,553 B1 | 10/2011 | Durcan | |
| 8,099,849 B2 | 1/2012 | Gale et al. | |
| 8,173,062 B1 | 5/2012 | Durcan | |
| 8,206,436 B2 | 6/2012 | Mangiardi et al. | |
| 8,211,163 B2 | 7/2012 | Dakin et al. | |
| 8,241,554 B1 | 8/2012 | Abbate et al. | |
| 8,252,215 B2 | 8/2012 | Wang | |
| 8,261,423 B2 | 9/2012 | Jow et al. | |
| 8,303,296 B2 | 11/2012 | Kleiner et al. | |
| 8,303,644 B2 | 11/2012 | Lord et al. | |
| 8,303,645 B2 | 11/2012 | Oepen et al. | |
| 8,323,329 B2 | 12/2012 | Gale et al. | |
| 8,388,673 B2 | 3/2013 | Yang et al. | |
| 8,539,663 B2 | 9/2013 | Wang et al. | |
| 9,198,782 B2 | 12/2015 | Kleine et al. | |
| 9,216,238 B2 * | 12/2015 | Huang | A61L 31/06 |
| 9,554,925 B2 | 1/2017 | Gale et al. | |
| 2001/0014821 A1 | 8/2001 | Juman et al. | |
| 2002/0035394 A1 | 3/2002 | Fierens et al. | |
| 2002/0041059 A1 | 4/2002 | Jung et al. | |
| 2002/0077592 A1 | 6/2002 | Barry | |
| 2002/0099438 A1 | 7/2002 | Furst | |
| 2002/0111590 A1 * | 8/2002 | Davila | A61B 17/0644 |
| | | | 604/265 |
| 2002/0138133 A1 | 9/2002 | Lenz et al. | |
| 2002/0151965 A1 | 10/2002 | Roth | |
| 2003/0023301 A1 | 1/2003 | Cox et al. | |
| 2003/0028241 A1 | 2/2003 | Stinson | |
| 2003/0028246 A1 | 2/2003 | Palmaz et al. | |
| 2003/0050687 A1 | 3/2003 | Schwade et al. | |
| 2003/0055488 A1 | 3/2003 | Igaki | |
| 2003/0083732 A1 | 5/2003 | Stinson | |
| 2003/0149470 A1 | 8/2003 | Alvarado et al. | |
| 2003/0181973 A1 * | 9/2003 | Sahota | A61F 2/91 |
| | | | 623/1.15 |
| 2003/0187158 A1 | 10/2003 | Preuschen et al. | |
| 2003/0208254 A1 | 11/2003 | Shortt | |
| 2003/0208259 A1 * | 11/2003 | Penhasi | A61L 31/146 |
| | | | 623/1.15 |

(56) References Cited

U.S. PATENT DOCUMENTS

| | | |
|---|---|---|
| 2003/0216804 A1* | 11/2003 | DeBeer ............... A61F 2/90 623/1.15 |
| 2003/0226833 A1 | 12/2003 | Shapovalov et al. |
| 2004/0000361 A1 | 1/2004 | Trozera |
| 2004/0015187 A1* | 1/2004 | Lendlein ......... A61B 17/06166 606/228 |
| 2004/0044400 A1 | 3/2004 | Cheng et al. |
| 2004/0088041 A1* | 5/2004 | Stanford ............. A61F 2/91 623/1.15 |
| 2004/0098090 A1 | 5/2004 | Williams et al. |
| 2004/0116332 A1* | 6/2004 | Ornberg ............. A61L 27/20 623/1.51 |
| 2004/0122184 A1* | 6/2004 | Mather ............ C08G 18/3893 525/387 |
| 2004/0127972 A1* | 7/2004 | Kitaoka ............. A61F 2/91 623/1.15 |
| 2004/0138738 A1* | 7/2004 | Stinson ............. A61F 2/90 623/1.38 |
| 2004/0167610 A1* | 8/2004 | Fleming, III ........ A61F 2/91 623/1.15 |
| 2004/0181271 A1 | 9/2004 | DeSimone et al. |
| 2004/0181277 A1* | 9/2004 | Furst ............... A61F 2/91 623/1.16 |
| 2004/0215326 A1 | 10/2004 | Goodson et al. |
| 2004/0220665 A1* | 11/2004 | Hossainy ............ A61L 27/34 623/1.42 |
| 2004/0260386 A1* | 12/2004 | Shalaby ............. A61F 2/86 623/1.15 |
| 2005/0004656 A1* | 1/2005 | Das ................. A61F 2/91 623/1.16 |
| 2005/0004659 A1 | 1/2005 | Von Oepen et al. |
| 2005/0004662 A1 | 1/2005 | Von Oepen et al. |
| 2005/0004663 A1 | 1/2005 | Llanos et al. |
| 2005/0102022 A1 | 5/2005 | Solovay et al. |
| 2005/0113909 A1* | 5/2005 | Shannon ............. A61F 2/07 623/1.46 |
| 2005/0119720 A1* | 6/2005 | Gale ............... A61F 2/958 623/1.11 |
| 2005/0131522 A1* | 6/2005 | Stinson ............. A61F 2/91 623/1.15 |
| 2005/0137678 A1 | 6/2005 | Varma |
| 2005/0149172 A1 | 7/2005 | Varma |
| 2005/0171596 A1* | 8/2005 | Furst ............... A61L 31/10 623/1.16 |
| 2005/0177130 A1 | 8/2005 | Konstantino et al. |
| 2005/0187615 A1 | 8/2005 | Williams et al. |
| 2005/0196485 A1 | 9/2005 | Cass et al. |
| 2005/0203617 A1 | 9/2005 | Forster et al. |
| 2005/0209680 A1* | 9/2005 | Gale ............... A61L 31/028 623/1.15 |
| 2006/0020330 A1 | 1/2006 | Huang et al. |
| 2006/0076708 A1 | 4/2006 | Huang et al. |
| 2006/0095115 A1 | 5/2006 | Bladillah et al. |
| 2006/0111771 A1* | 5/2006 | Ton ................. A61F 2/88 623/1.15 |
| 2006/0136040 A1 | 6/2006 | Burgermeister et al. |
| 2006/0211952 A1 | 9/2006 | Kennedy |
| 2006/0224226 A1 | 10/2006 | Huang et al. |
| 2006/0235506 A1* | 10/2006 | Ta ................. A61F 2/91 623/1.16 |
| 2006/0241739 A1* | 10/2006 | Besselink ........... A61B 17/11 623/1.15 |
| 2006/0259122 A1 | 11/2006 | Eliseev |
| 2006/0265048 A1* | 11/2006 | Cheng .............. A61F 2/91 623/1.15 |
| 2006/0265050 A1 | 11/2006 | Morris et al. |
| 2007/0034615 A1* | 2/2007 | Kleine ............... A61F 2/91 219/121.72 |
| 2007/0038290 A1* | 2/2007 | Huang .............. A61F 2/90 623/1.16 |
| 2007/0045252 A1* | 3/2007 | Kleine ............... B23K 26/38 219/121.69 |
| 2007/0045255 A1* | 3/2007 | Kleine ............... B23K 26/38 219/121.72 |
| 2007/0073016 A1 | 3/2007 | Alvarado et al. |
| 2007/0073376 A1 | 3/2007 | Krolik et al. |
| 2007/0135892 A1 | 6/2007 | Burgermeister et al. |
| 2007/0135896 A1 | 6/2007 | Burgermeister et al. |
| 2007/0135898 A1 | 6/2007 | Burgermeister et al. |
| 2007/0135899 A1 | 6/2007 | Burgermeister et al. |
| 2007/0135983 A1 | 6/2007 | McDonald et al. |
| 2007/0135985 A1 | 6/2007 | Berry et al. |
| 2007/0142903 A1* | 6/2007 | Dave ............... B23K 26/0648 623/1.22 |
| 2007/0151961 A1* | 7/2007 | Kleine ............... B23K 26/073 219/121.72 |
| 2007/0156226 A1 | 7/2007 | Chew et al. |
| 2007/0200229 A1 | 8/2007 | Daubenspeck et al. |
| 2007/0213810 A1 | 9/2007 | Newhauser et al. |
| 2007/0216619 A1 | 9/2007 | Hung |
| 2007/0228023 A1* | 10/2007 | Kleine ............... B23K 26/0626 219/121.67 |
| 2007/0253996 A1 | 11/2007 | Bin et al. |
| 2007/0253999 A1 | 11/2007 | Huang et al. |
| 2007/0265698 A1 | 11/2007 | Pienknagura |
| 2007/0271763 A1 | 11/2007 | Huang et al. |
| 2007/0282431 A1 | 12/2007 | Gale et al. |
| 2007/0282433 A1* | 12/2007 | Limon ............... A61F 2/91 623/1.38 |
| 2007/0283552 A1* | 12/2007 | Gale ............... A61F 2/91 29/515 |
| 2007/0290412 A1 | 12/2007 | Capek et al. |
| 2007/0293938 A1* | 12/2007 | Gale ............... A61F 2/91 623/1.15 |
| 2008/0001333 A1 | 1/2008 | Kleine et al. |
| 2008/0009938 A1* | 1/2008 | Huang .............. A61F 2/91 623/1.38 |
| 2008/0147164 A1 | 6/2008 | Gale et al. |
| 2008/0177373 A1 | 7/2008 | Huang et al. |
| 2008/0177374 A1* | 7/2008 | Zheng .............. A61L 31/06 623/1.15 |
| 2008/0275537 A1 | 11/2008 | Limon |
| 2008/0300670 A1* | 12/2008 | Gueriguian .......... A61F 2/91 623/1.15 |
| 2009/0001633 A1 | 1/2009 | Limon et al. |
| 2009/0005854 A1 | 1/2009 | Huang et al. |
| 2009/0005860 A1 | 1/2009 | Huang et al. |
| 2009/0012598 A1 | 1/2009 | Abbate et al. |
| 2009/0146348 A1 | 6/2009 | Huang et al. |
| 2009/0216311 A1 | 8/2009 | Flagle et al. |
| 2009/0264979 A1 | 10/2009 | Kao et al. |
| 2010/0004735 A1 | 1/2010 | Yang et al. |
| 2010/0025894 A1 | 2/2010 | Kleiner et al. |
| 2010/0174358 A1 | 7/2010 | Rabkin et al. |
| 2010/0204778 A1 | 8/2010 | LaFont et al. |
| 2010/0217373 A1 | 8/2010 | Boyle et al. |
| 2010/0256736 A1 | 10/2010 | Purdy et al. |
| 2010/0256740 A1 | 10/2010 | Limon et al. |
| 2010/0274349 A1 | 10/2010 | Lord et al. |
| 2010/0289191 A1 | 11/2010 | Gale et al. |
| 2010/0323091 A1 | 12/2010 | Castro et al. |
| 2011/0066222 A1 | 3/2011 | Wang et al. |
| 2011/0066225 A1* | 3/2011 | Trollsas ............. A61F 2/91 623/1.16 |
| 2011/0112627 A1 | 5/2011 | Gale et al. |
| 2011/0172759 A1 | 7/2011 | Schmid et al. |
| 2011/0190871 A1 | 8/2011 | Trollsas et al. |
| 2011/0190872 A1 | 8/2011 | Anukhin et al. |
| 2011/0224778 A1 | 9/2011 | Gale et al. |
| 2011/0230959 A1 | 9/2011 | Pienknagura |
| 2011/0245904 A1 | 10/2011 | Pacetti et al. |
| 2011/0260352 A1 | 10/2011 | Tang et al. |
| 2011/0270383 A1 | 11/2011 | Jow et al. |
| 2011/0270384 A1 | 11/2011 | Lord |
| 2011/0271513 A1 | 11/2011 | Wang |
| 2011/0278771 A1 | 11/2011 | Kleiner et al. |
| 2012/0042501 A1 | 2/2012 | Wang et al. |
| 2012/0073733 A1 | 3/2012 | Ngo et al. |
| 2012/0271896 A1 | 10/2012 | Zheng et al. |
| 2012/0285609 A1 | 11/2012 | Wang |

(56) References Cited

U.S. PATENT DOCUMENTS

| | | |
|---|---|---|
| 2012/0299226 A1 | 11/2012 | Wang et al. |
| 2012/0316635 A1 | 12/2012 | Jow et al. |
| 2012/0319333 A1 | 12/2012 | Huang et al. |
| 2012/0330403 A1 | 12/2012 | Gomez et al. |
| 2013/0026681 A1 | 1/2013 | Kleiner et al. |
| 2013/0150943 A1 | 6/2013 | Zheng et al. |
| 2013/0181380 A1 | 7/2013 | Yang et al. |
| 2013/0255853 A1 | 10/2013 | Wang et al. |

FOREIGN PATENT DOCUMENTS

| | | |
|---|---|---|
| EP | 1 859 823 | 11/2007 |
| EP | 2 152 207 | 11/2008 |
| GB | 2 102 827 | 2/1983 |
| WO | WO 97/32546 | 9/1997 |
| WO | WO 00/12147 | 3/2000 |
| WO | WO 01/15633 | 3/2001 |
| WO | WO 03/034940 | 5/2003 |
| WO | WO 2004/067262 | 8/2004 |
| WO | WO 2006/014747 | 2/2006 |
| WO | WO 2007/021706 | 2/2007 |
| WO | WO 2007/142750 | 12/2007 |
| WO | WO 2007/146354 | 12/2007 |
| WO | WO 2007/149457 | 12/2007 |

OTHER PUBLICATIONS

International Search Report for PCT/US2008/062607, dated Aug. 5, 2008, 6 pgs.
European Search Report for appl. No. 08 747619.8, dated Sep. 27, 2011, 5 pgs.
Translation of Notice of Reason for Rejection for JP appl. No. 2010-506710, dispatched Sep. 25, 2012, 3 pgs.
Angioplasty Summit Abstracts/Oral, The Am. J. of Cardiology, Apr. 23-26, 2013, p. 23B.
Answers.com blow molding; retrieved from www.answers.com/blow%20molding#Stretch_blow_molding, Jun. 26, 2009, 11 pgs.
Bosiers et al., "Coronary and endovascular applications of the Absorb™ bioresorbable vascular scaffold", Interv. Cardiol. 4(6), pp. 621-631 (2012).
Declaration under 37 C.F.R. § 1.132 by Bin Huang and David Gale filed in U.S. Appl. No. 11/417,376, executed Jul. 22, 2010, 5 pgs.
International Search Report for PCT/US2007/013915 filed Jun. 13, 2007, dated Jan. 7, 2008, 4 pgs.
Middleton et al., Synthetic Biodegradable Polymers as Medical Devices, Medical Device and Diagnostic Industry; downloaded from www.mddionline.com/article/synthetic-biodegradable-polymers-medical-devices, Mar. 1998, 4 pgs.
Miller "Abbott's Bioresorbable Stent Shows Durable Results in ABSORB Trial", The Gray Sheet, pp. 17-18, Mar. 2003.
www.engineeringtoolbox.com/thermal/conductivity/d_429.html., Jun. 26, 2009, 4 pgs.

\* cited by examiner

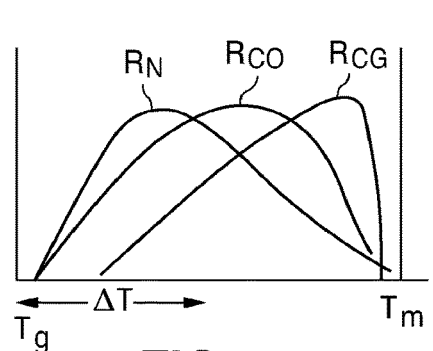
FIG. 4
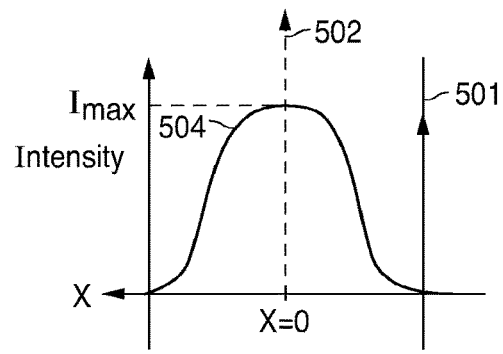
FIG. 5
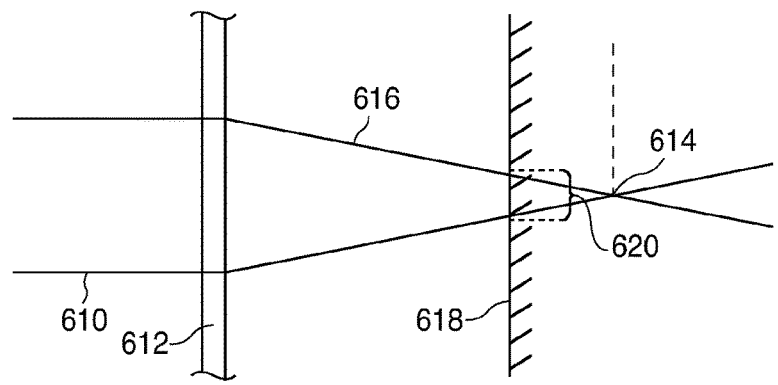
FIG. 6
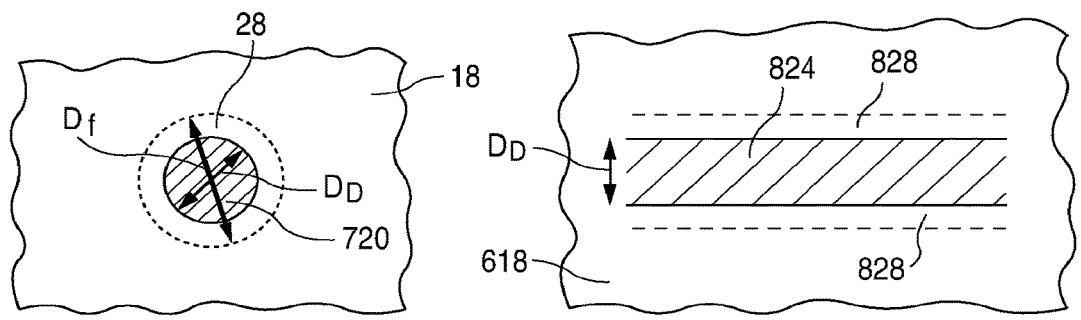
FIG. 7  FIG. 8

MANUFACTURING PROCESS FOR POLYMERIC STENTS

CROSS REFERENCE TO RELATED APPLICATIONS

This application is a division of U.S. application Ser. No. 14/255,896 filed Apr. 17, 2014, now U.S. Pat. No. 9,554,925, which is a continuation of U.S. application Ser. No. 14/252,689 filed Apr. 14, 2014, now U.S. Pat. No. 9,198,782, which is a continuation of U.S. application Ser. No. 13/112,960 filed May 20, 2011, now abandoned, which is a continuation of U.S. application Ser. No. 11/443,947 filed on May 30, 2006, now U.S. Pat. No. 7,971,333, all of which are incorporated by reference herein.

BACKGROUND OF THE INVENTION

Field of the Invention

This invention relates to methods of manufacturing polymeric stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodible materials such as bioabsorbable polymers can be designed to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

SUMMARY OF THE INVENTION

Certain embodiments of the invention include a method of fabricating a stent delivery device comprising forming a polymeric tube using extrusion, the tube being drawn during extrusion so that a diameter of the formed tube is less than a target diameter; radially deforming the formed tube so that the deformed tube comprises the target diameter; forming a stent from the deformed tube, wherein forming the stent includes laser machining a stent pattern in the deformed tube with an ultra-short pulse laser; and crimping the stent on a support element, wherein a temperature of the stent during crimping is above an ambient temperature.

BRIEF DESCRIPTION OF THE DRAWINGS

FIG. 4 depicts a schematic plot of the crystal nucleation rate and the crystal growth rate, and the overall rate of crystallization.

FIG. 5 depicts a mathematical representation of a Gaussian laser beam profile.

FIG. 6 depicts a collimated two-dimensional representation of a laser beam.

FIG. 7 depicts an overhead view of the surface of a substrate.

FIG. 8 illustrates a kerf machined by a laser.

DETAILED DESCRIPTION OF THE INVENTION

Various embodiments of methods of manufacturing a polymeric stent and a delivery system for a stent are disclosed. A stent can be made of a biostable, biodegradable, or a combination of a biostable and biodegradable polymer. The terms degrade, absorb, and erode, as well as degraded, eroded, and absorbed, are used interchangeably and refer to materials that are capable of being completely eroded, or absorbed when exposed to bodily conditions.

Figure 1:
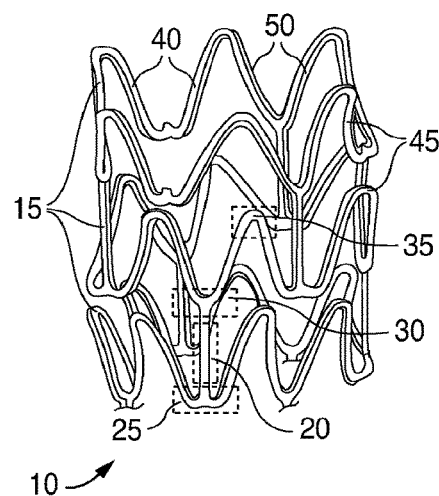
FIG. 1 depicts a stent.

A stent may include a pattern or network of interconnecting structural elements or struts. FIG. 1 depicts an example of a three-dimensional view of a stent 10. The stent may have a pattern that includes a number of interconnecting elements or struts 15. The embodiments disclosed herein are not limited to stents or to the stent pattern illustrated in FIG. 1.

The embodiments described herein are easily applicable to other patterns and other implantable medical devices, including, but not limited to self-expandable stents, balloon-expandable stents, stent-grafts, and grafts. The structural pattern of the device can be of virtually any design. The variations in the structure of patterns are virtually unlimited. As shown in FIG. 1 the geometry or shape of stents vary throughout its structure. A pattern may include portions of struts that are straight or relatively straight, an example being a section 20. Patterns may also include intersections of struts with curved or bent portions or elements as in sections 25 and 30. In addition, patterns may include struts that include curved or bent portions or elements as in a section 35.

Additionally, a surface of a medical device, such as a stent, may also be characterized by the relative location of the surface with respect to a bodily lumen. The stent includes abluminal surfaces or outer portions, luminal surfaces or inner portions, and surfaces between the abluminal and luminal surfaces. For example, struts 15 of stent 10 include luminal faces or surfaces 40, abluminal faces or surfaces 45, and side-wall faces or surfaces 50.

A stent such as stent 10 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from about a month to a few years. However, the duration is typically up to about six months, twelve months, eighteen months, or two years. In some situations, the treatment period can extend beyond two years. Stents composed of biodegradable polymers are particularly attractive since they can be designed to remain in the body during the above-mentioned time frames.

In addition, to biodegradability, there are several properties that are generally desirable for a stent to have that greatly facilitate the delivery, deployment, and treatment of a diseased vessel. As indicated above, a stent has certain mechanical requirements. A stent must have sufficient radial strength to withstand structural loads, namely radial compressive forces, imposed on the stent as it supports the walls of a vessel. In addition, the stent must possess sufficient flexibility to allow for crimping, expansion, and cyclic loading. Also, a sufficiently low profile, that includes diameter and size of struts, is important. As the profile of a stent decreases, the easier is its delivery, and the smaller the disruption of blood flow.

Polymers tend to have a number of shortcomings for use as materials for stents. One such shortcoming is that many biodegradable polymers have a relatively low modulus, and thus relatively low radial strength. Compared to metals, the strength to weight ratio of polymers is smaller than that of metals. A polymeric stent with inadequate radial strength can result in mechanical failure or recoil inward after implantation into a vessel. To compensate for the relatively low modulus, a polymeric stent requires significantly thicker struts than a metallic stent, which results in an undesirably large profile.

Another shortcoming of polymers is that many polymers, such as biodegradable polymers, tend to be brittle under biological conditions or conditions within a human body. Specifically, such polymers can have a Tg above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

Other potential problems with polymeric stents include creep, stress relaxation, and physical aging. Creep refers to the gradual deformation that occurs in a polymeric construct subjected to an applied load. Creep occurs even when the applied load is constant.

It is believed that the delayed response of polymer chains to stress during deformation causes creep behavior. As a polymer is deformed, polymeric chains in an initial state rearrange to adopt a new equilibrium configuration. Rearrangement of chains takes place slowly with the chains retracting by folding back to their initial state. For example, an expanded stent can retract radially inward, reducing the effectiveness of a stent in maintaining desired vascular patency. The rate at which polymers creep depends not only on the load, but also on temperature. In general, a loaded construct creeps faster at higher temperatures.

Stress relaxation is also a consequence of delayed molecular motions as in creep. Contrary to creep, however, which is experienced when the load is constant, stress relaxation occurs when deformation (or strain) is constant and is manifested by a reduction in the force (stress) required to maintain a constant deformation. The mechanism responsible for both stress relaxation and creep will result in recoil, as the stent may experience deformation in response to an applied load (from the vessel). Unlike stress relaxation, the deformation imposed on the stent may change with time. Unlike creep, the applied load will also change with time.

Physical aging, as used herein, refers to densification in the amorphous regions of a semi-crystalline polymer. Densification is the increase in density of a material or region of a material. Densification results from residual and applied stresses. As used herein, a "residual stress" includes, without limitation, the stress in a bulk polymer that is in a non-equilibrium thermodynamic state. Physical aging of semi-crystalline polymers that have glass transition temperatures (Tg) above their normal storage temperature, which, for the purposes of this invention is room temperature, i.e., from about 15° C. to about 35° C., occurs primarily through the phenomenon known as densification.

Densification occurs when a semi-crystalline polymer is cooled at a non-equilibrium rate from a temperature above its Tg to a temperature below its Tg. Non-equilibrium cooling is normally what will occur in most industrial settings since equilibrium cooling is very slow and would be considered economically impractical. The non-equilibrium cooling rate results in the polymer chains of the amorphous domains being trapped at non-optimal separation distances in the glassy state that forms when the temperature goes below Tg. The chains then attempt to achieve optimal separation by coordinated localized chain motion. The reordering of polymer chains tends to increase the modulus of the polymer resulting in a brittle or more brittle polymer. Thus, densification of a polymer initially selected for its toughness and elasticity could cause failure of a coating or polymeric scaffolding when the polymer ages or densifies and becomes brittle.

Certain embodiments of the present invention relate to methods of fabricating a polymeric stents that have one or more above-mentioned required or desirable properties including biodegradability, adequate toughness in the conditions of use of a stent, and a strength to weight ratio close to metals resulting in an acceptable stent profile. The embodiments can also reduce or eliminate above mentioned shortcomings of polymeric materials such as creep, stress relaxation, and physical aging.

In certain embodiments, a method of forming a stent may include forming a tube and laser machining a tube to form a stent pattern in a manner that the formed stent has the above-mentioned required or desirable properties. Certain embodiments of a method of fabricating a stent may include:

(1) forming a polymeric tube using extrusion,
(2) radially deforming the formed tube, and
(3) forming a stent from the deformed tube by laser machining a stent pattern in the deformed tube with an ultra-short pulse laser.

In some embodiments, the tubing can be extruded to dimensions that allow radial deformation of the tube to a desired size for fabrication of a stent. Radial deformation tends to increase the radial strength of the tubing, and the subsequently fabricated stent. Additionally, the tube can be extruded so that the resultant tube has relatively low crystallinity which reduces brittle behavior and increases toughness.

Other embodiments of a method of fabricating a polymeric stent can include one or more of the following of the additional features:

(1) the method can include the use of an ultrafast laser reduces the deleterious affects on mechanical properties of the polymer during laser machining, (2) the method can include forming a stent pattern in which the strain experienced by the stent is spread or distributed over a relatively large area rather than being highly concentrated when the stent is deformed, and (4) embodiments can include fabricating the stent from a semicrystalline polymer which can reduce or eliminate creep, stress relaxation, and physical aging.

Further embodiments can include fabricating a stent delivery device by crimping the stent on a support element such that the temperature of the stent during crimping is above an ambient temperature. Heating a stent during crimping can reduce or eliminate radially outward recoiling of a crimped stent which can result in an unacceptable profile for delivery.

Polymer tubes may be formed using various types of forming methods, including, but not limited to extrusion or injection molding. Alternatively, a polymer tube may be formed from sheets that are rolled and bonded into a tube. Representative examples of extruders include, but are not limited to, single screw extruders, intermeshing co-rotating and counter-rotating twin-screw extruders and other multiple screw masticating extruders.

In extrusion, a polymer melt is conveyed through an extruder and forced through a die in the shape of as an annular film in the shape of a tube. The annular film can be cooled below the melting point, Tm, of the polymer to form an extruded polymeric tube.

In one embodiment, the annular film in the shape of a tube can be axially drawn or stretched. As the tube is drawn, its diameter decreases. Therefore, the tube can be drawn to have a selected diameter. In some embodiments, the annular film may be drawn by a puller. The puller may include a conveyor assembly that supports and sizes the annular film.

The annular film may be cooled during expansion and/or after drawing. For example, the annular film may be conveyed through a water bath at a selected temperature. Alternatively, the annular film may be cooled by air at a selected temperature. The annular film may be cooled at or near an ambient temperature, e.g. 25° C. Alternatively, the annular film may be cooled at a temperature below ambient temperature.

As mentioned above, polymers tend of have a relatively low strength to weight ratio as compared to metals. Fabrication of a polymeric stent with strength comparable to a conventional metallic stent can require undesirably large struts.

Thus, in certain embodiments, a method of fabricating a stent may include modifying the mechanical properties of polymer construct, such as a tube, to have desirable mechanical properties. The polymer can be modified to increase the strength, modulus, and/or toughness of the polymer tube. In some embodiments, the polymer can be modified to allow fabrication of a polymeric stent with strength comparable to a conventional metallic stent and with strut dimensions that are close to the dimensions of conventional metallic stents.

It is well known by those skilled in the art that the mechanical properties of a polymer can be modified by applying stress to a polymer. The strength and modulus of a polymer can be increased along the direction of the applied stress. The application of stress can induce molecular orientation along the direction of stress which can increase the strength and modulus along the direction. Molecular orientation refers to the relative orientation of polymer chains along a longitudinal or covalent axis of the polymer chains.

Molecular orientation can be induced in polymers that are completely amorphous, partially or semi-crystalline, or almost completely crystalline. A partially or semi-crystalline polymer includes crystalline regions separated by amorphous regions. The crystalline regions do not necessarily have the same or similar orientation of polymer chains. However, a high degree of orientation of crystallites may be induced by applying stress to a semi-crystalline polymer. The stress may also induce orientation in the amorphous regions.

Due to the magnitude and directions of stresses imposed on a stent during use, it is important for the mechanical stability of a device to have an adequate magnitude of strength both in axial and circumferential directions. Therefore, an adequate balance of axial and circumferential strength is also important for mechanical stability. The relative amount of axial and circumferential orientation may depend on a number of factors such as the stent pattern, initial diameter of the tube, final diameter of the stent, and crimped diameter of the stent. Polymer tubes formed by extrusion methods tend to possess a significant degree of axial polymer chain alignment. However, such conventionally extruded tubes tend to possess no or substantially no polymer chain alignment in the circumferential direction.

Some embodiments of a method of fabricating a stent may include radially deforming a polymeric tube about a cylindrical axis of the tube. The tube can be radially deformed to increase the strength and modulus in the circumferential direction. The increase in strength and modulus can be due to the induced molecular orientation in the circumferential direction.

Additionally, the method may further include axially deforming the tube along the cylindrical axis of the tube. In one embodiment, the tube may be axially deformed by applying a tensile force to the tube along the cylindrical axis. Axial deformation of the polymer tube may induce axial molecular orientation, and hence, increase the axial strength and modulus or rigidity. Various embodiments may include radially deforming the tube prior to, subsequent to, and/or contemporaneously with axial deformation the tube.

The degree of polymer chain alignment induced with applied stress may depend upon the temperature of the polymer. Above Tg, polymer chain alignment may be readily induced with applied stress since polymer chains have greater mobility than below Tg. Consequently, the amount of deformation depends on the temperature of a polymeric material. Therefore, it is advantageous to radially deform the tube at a temperature above Tg.

Additionally, the polymeric tube may be heat set to allow polymeric chains to rearrange upon deformation. "Heat setting," as used herein, refers to maintaining a polymer at an elevated temperature to allow polymer chains in the heated polymer to move toward a state of thermodynamic equilibrium. In a deformed polymeric tube, polymeric chains are allowed to equilibrate towards the induced highly oriented structure at the elevated temperature. Since polymer chain alignment is a time and temperature dependent process, a highly oriented structure that is thermodynamically stable at a given temperature may not be formed instantaneously. Thus, the polymeric tube may be maintained in a deformed state at an elevated temperature for a period of time.

Figure 2:
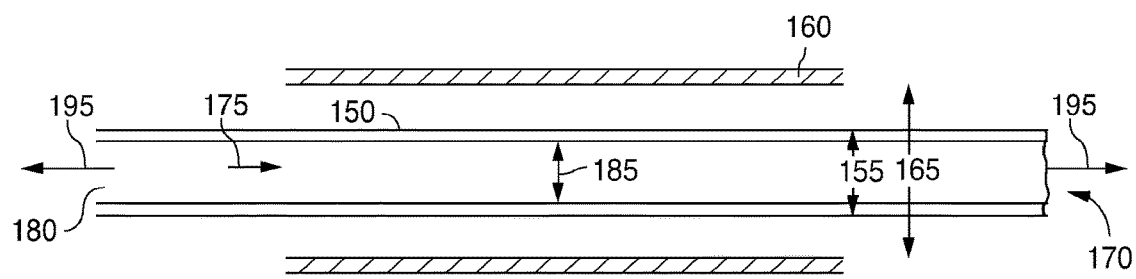
FIG. 2 depicts an axial cross-section of a polymer tube positioned within an annular member or mold.
Figure 3:
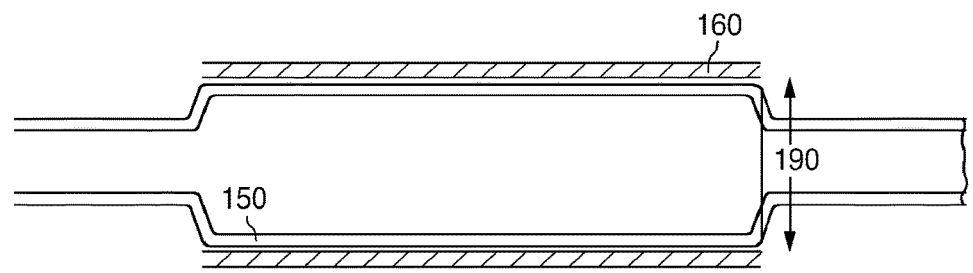
FIG. 3 depicts a deformed polymer tube in a mold.

A tube can be radially deformed using blow molding. FIGS. 2 and 3 illustrate an embodiment of deforming a polymeric tube in manufacturing a stent. FIG. 2 depicts an axial cross-section of a polymeric tube 150 with an outside diameter 155 positioned within an annular member or mold 160. Mold 160 may act to limit the radial deformation of polymeric tube 150 to a diameter 165, the inside diameter of mold 160. Polymer tube 150 may be closed at a distal end 170. Distal end 170 may be open in subsequent manufacturing steps. A fluid may be conveyed, as indicated by an arrow 175, into an open proximal end 180 of polymeric tube 150. A tensile force 195 is applied at proximal end 180 and a distal end 170.

Polymeric tube 150 may be heated by heating the gas to a temperature above ambient temperature prior to conveying the gas into polymeric tube 150. Alternatively, the polymeric tube may be heated by heating the exterior of mold 160. The tube may also be heated by the mold. The increase in pressure inside of polymer tube 150 facilitated by an increase in temperature of the polymeric tube causes radial deformation of polymer tube 150, as indicated by an arrow 185. FIG. 3 depicts polymeric tube 150 in a deformed state with an outside diameter 190 within annular member 160.

Additionally, as indicated above, the pressure inside the tube and the temperature of the tube may be maintained at the elevated temperature for a period of time to allow the polymeric tube to be heat set. The period of time may be between about one minute and about two hours, or more narrowly, between about two minutes and about ten minutes.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Outside Diameter of Deformed Tube}}{\text{Original Inside Diameter of Tube}}$$

In some embodiments, the radial draw ratio of a polymeric tube for use in fabricating a stent may be between about 1 and 20, or more narrowly between about 2 and 6. Similarly, the degree of axial deformation may be quantified by an axial draw ratio:

$$\frac{\text{Length of Deformed Tube}}{\text{Original Length of Tube}}$$

In some embodiments, a stent can be fabricated from the radially expanded tube by laser machining. The stent may then be crimped on to a delivery device such as a balloon. Therefore, the extruded tube must have a diameter that is less than a target diameter, the target diameter corresponding to a diameter at which a stent pattern is formed by laser machining or a diameter of a stent prior to crimping. Thus, the extruded tube can then be radially expanded to the target diameter.

The degree of induced strength due to radial expansion depends on the amount of radial expansion as quantified by the blow-up ratio. Thus, the degree of radial expansion is determined by the extruded diameter and the target diameter. In some embodiments, the extruded diameter can be used to determine the degree of radial expansion. The smaller the extruded diameter, the larger is the degree of radial expansion. In some embodiments, the extruded diameter can be controlled by the drawing of the polymer film as it exits the die. For a die having a diameter similar to the target diameter, the axial draw down ratio can be between 1 and 3. The axial drawdown ratio is defined as:

$$\frac{\text{Drawn Length of Tube}}{\text{Original Length of Tube}}$$

In further embodiments, it may be desirable to control the degree of crystallinity in a polymer tube during extrusion, radial deformation, and/or axial deformation to reduce or eliminate physical aging, creep, and stress relaxation in a stent. Additionally, it is also desirable to control crystallinity to increase the toughness of a stent.

As discussed above, physical aging, creep, and stress relaxation are due at least in part to rearrangement of polymer chains in amorphous regions of a polymer. Thus, as crystallinity increases in a polymer, physical aging, creep, and stress relaxation tend to reduced. Therefore, it is advantageous to use crystalline or semi-crystalline polymers for a stent to reduce or eliminate physical aging, creep, and stress relaxation.

However, crystalline and semi-crystalline polymers can be relatively brittle at biological conditions, i.e., the temperature of the human body. In particular, such polymers can have a Tg below the body temperature. These polymers can have a low fracture toughness and are thus susceptible to mechanical failure during use, for example, during crimping, deployment, and treatment. It is important for a stent to have a high fracture toughness throughout the range of stress experienced during use. For a semi-crystalline polymer, the higher the crystallinity, the more likely the polymer will be brittle under biological conditions.

Semi-crystalline polymers can contain both amorphous and crystalline domains at temperatures below their melting point. Amorphous regions are those in which polymer chains are in relatively disordered configurations. Crystalline domains are those in which polymer chains are in ordered configurations with segments of polymer chains essentially parallel to one another.

In certain embodiments, the crystallinity of an extruded tube can be controlled by controlling the temperature of cooling the annular film exiting the die. In general, crystallization tends to occur in a polymer at temperatures between Tg and Tm of the polymer. The rate of crystallization in this range varies with temperature. FIG. 4 depicts a schematic plot of the crystal nucleation rate ($R_N$), the crystal growth rate ($R_{CG}$), and the overall rate of crystallization ($R_{CO}$). The crystal nucleation rate is the growth rate of new crystals and the crystal growth rate is the rate of growth of formed crystals. The overall rate of crystallization is the sum of curves $R_N$ and $R_{CG}$.

In certain embodiments, the temperature of the annular tube exiting the extruder during cooling can be at a temperature at which the overall crystallization rate is relatively low. In some embodiments, the temperature can be in a range in which the crystal nucleation rate is larger than the crystal growth rate. In one embodiment, the temperature can be in a range in which the crystal nucleation rate is substantially larger than the crystal growth rate. For example, the temperature can be where the ratio of the crystal nucleation rate to crystal growth rate is 2, 5, 10, 50, 100, or greater than 100. In another embodiment, the temperature range may be in range, ΔT shown in FIG. 4, between about Tg to about 0.5 (Tm−Tg)+Tg.

The resulting polymeric tube may then have relatively low crystallinity. Additionally, since the nucleation rate is higher than the crystal growth rate, the resulting polymer can have a relatively large number of crystalline domains that are relatively small. As the size of the crystalline domains decreases along with an increase in the number of domains, the polymer may become less brittle and, thus, which increases the fracture toughness.

Although the crystallinity of the resulting polymer can be relatively low, the presence of the relatively large number of relatively small crystalline domains can reduce or eliminate physical aging, creep, and stress relaxation. It is believed that crystallites inhibit movement of polymer chains in the amorphous regions. As indicated above, such movement contributes to physical aging, creep, and stress relaxation.

Additionally, crystallinity in a polymeric tube can also be controlled during radial deformation to increase fracture toughness and reduce physical aging, creep, and stress relaxation. As indicated above, it is desirable to radial deform at a temperature above a Tg of the polymer to facilitate deformation and to heat set the polymer above the Tg. As a result, crystallization tends to occur in the polymer during deformation and heat setting. In addition, crystallinity in addition to orientation may be induced in the polymer during deformation. This process is referred to as strain-induced crystallization.

Thus, embodiments of the method can include radially deforming and/or heat setting in temperature ranges described above for extrusion. Deforming and heat setting a tube in such a temperature range can result in a radially deformed tube with a higher fracture toughness and reduced physical aging, creep, and stress relaxation for the same reasons as explained above for extrusion.

In other embodiments, an extruded tube can be formed that is amorphous or substantially amorphous. An amorphous polymeric tube can be formed by quenching the annular tube exiting the die so that its temperature is reduced to a temperature from above Tm to below Tg so that no or substantially no crystallization occurs in the polymer during cooling. Thus, an amorphous glassy polymer can be formed. The tube can then be deformed and heat set, as described above, at a temperature that results in high fracture toughness and with reduced physical aging, creep, and stress relaxation.

Additionally, certain embodiments of a method of fabricating a stent can include laser machining a stent pattern in an extruded and radially deformed tube. In some embodiments, a stent pattern may be formed with an ultrashort-pulse lasers. "Ultrashort-pulse lasers" refer to lasers having pulses with durations shorter than about a picosecond ($=10^{-12}$). Ultrashort-pulse lasers can include both picosecond and femtosecond ($=10^{-15}$) lasers. The ultrashort-pulse laser is clearly distinguishable from conventional continuous wave and long-pulse lasers (nanosecond ($10^{-9}$) laser) which have significantly longer pulses. Certain embodiments of the present method may employ femtosecond lasers having pulses shorter than about $10^{-13}$ second.

The ultrashort-pulse lasers are known to artisans. For example, they are thoroughly disclosed by M. D. Perry et al. in Ultrashort-Pulse Laser Machining, Section K-ICALEO 1998, pp. 1-20. Representative examples of femtosecond lasers include, but are not limited to a Ti:sapphire laser (735 nm-1035 nm) and an excimer-dye laser (220 nm-300 nm, 380 nm-760 nm).

A significant advantage of ultra-short lasers as compared to longer pulse lasers is that ultra-short lasers tend to result in a significantly smaller heat affected zone (HAZ). A HAZ refers to a portion of a target substrate that is not removed, but is still exposed to energy from the laser beam, either directly or indirectly. Direct exposure may be due to exposure to the substrate from a section of the beam with an intensity that is not great enough to remove substrate material through either a thermal or nonthermal mechanism. For example, the portions of a beam near its edges may not have an intensity sufficiently high to remove substrate material. Most laser beams have a spatially uneven or nonuniform beam intensity profile, for example, a Gaussian beam profile. A substrate can also be exposed to energy indirectly due to heat conduction.

A heat affected zone in a target substrate is undesirable for a number of reasons. In polymers, heat can cause thermal distortion and roughness at the machined surface. The heat can also alter properties of a polymer such as mechanical strength and degradation rate. The heat can also cause chemical degradation that can affect the mechanical properties and degradation rate.

Additionally, heat can modify molecular structure of a polymer, such as degree of crystallinity and polymer chain alignment. Mechanical properties are highly dependent on molecular structure. As mentioned above, a high degree of crystallinity and/or polymer chain alignment is associated with a stiff, high modulus material. Heating a polymer above its melting point can result in an undesirable increase or decrease in crystallinity once the polymer resolidifies. Melting a polymer may also result in a loss of polymer chain alignment induced by radial expansion, which can adversely affect mechanical properties.

In addition, since heat from the laser modifies the properties of the substrate locally, the mechanical properties may become spatially nonuniform. Such nonuniformity may lead to mechanical instabilities such as cracking.

Longer-pulse lasers remove material from a surface principally through a thermal mechanism. The laser energy that is absorbed results in a temperature increase at and near the absorption site. As the temperature increases to the melting or boiling point, material is removed by conventional melting or vaporization. Depending on the pulse duration of the laser, the temperature rise in the irradiated zone may be very fast, resulting in thermal ablation and shock. An advantage of ultrashort-pulse lasers over longer-pulse lasers is that the ultrashort-pulse deposits its energy so fast that is does not interact with the plume of vaporized material, which would distort and bend the incoming beam and produce a rough-edged cut.

Unlike long-pulse lasers, ultrashort-pulse lasers allow material removal by a nonthermal mechanism. Extremely precise and rapid machining can be achieved with essentially no thermal ablation and shock. The nonthermal mechanism involves optical breakdown in the target material which results in material removal. As discussed below, optical breakdown may also occur with a gas, in particular with a process gas in contact with the beam at the surface of the target substrate. Optical breakdown tends to occur at a certain threshold intensity of laser radiation that is material dependent. Specifically each material has its own laser-induced optical breakdown threshold which characterizes the intensity required to ablate the material at a particular pulse width.

During optical breakdown of material, a very high free electron density, i.e., plasma, is produced. The plasma can be produced through mechanisms such as multiphoton absorption and avalanche ionization.

In optical breakdown, a critical density plasma is created in a time scale much shorter than electron kinetic energy is transferred to the substrate lattice. The resulting plasma is far from thermal equilibrium. The target material is converted from its initial solid-state directly into a fully ionized plasma on a time scale too short for thermal equilibrium to be established with a target material lattice. Therefore, there is negligible heat conduction beyond the region removed. As a result, there is negligible thermal stress or shock to the material beyond approximately 1 micron from the laser machined surface.

In laser machining with longer-pulse and ultra-fast pulse lasers, material removal tends to occur in an area or region of direct interaction of a laser beam with the target material or substrate. Laser machining typically involves focusing a laser beam onto an area or region of the substrate. The area of direct interaction corresponds to a focus diameter ($D_f$) on the target material that can be calculated from:

$$D_f = 1.27 * f * \lambda / D$$

where f is the focal length of a focusing optic, $\lambda$ is the wave length of the laser, and D is the beam diameter on the optic.

FIG. 5 depicts an axial cross-section of a laser beam 501 traveling in the "z" direction as indicated by an arrow 502. A mathematical representation 504 in the form of a Gaussian beam profile is shown superimposed on the beam. The profile has a maximum intensity ($I_{max}$) at the beam center (x=0) and then decreases with distance on either side of the maximum. The sections of the beam close to the edge may not remove material. However, such sections may still deposit energy into the material that can have undesirable thermal affects. Additionally, a portion of the substrate may also be heated through conduction.

FIGS. 6-8 are schematic illustrations of laser machining a substrate. FIG. 6 depicts a collimated two-dimensional representation of a laser beam 610 passing through a focusing lens 612 with a focal point 614. A focused laser beam 616 decreases in diameter with distance from lens 612. Beam 616 impinges on a substrate 618. The region of direct interaction of the laser beam has a diameter $D_f$.

FIG. 7 depicts an overhead view of the surface of substrate 618 showing region 720 with a diameter $D_D$ which corresponds to an area in which material is removed from the substrate. Region 720 is smaller than the area of direct interaction of the laser which has a diameter $D_f$. FIG. 8 illustrates that translation of the laser beam or substrate allows the laser beam to cut a trench or kerf 824 with at least a width $D_D$. Energy is deposited in region 828, but does not remove material. Region 828 corresponds to a portion of a heat affected zone. The heat affected zone can extend beyond region 828 since substrate material can also be heated by heat conduction.

Assemblies for laser machining stents have been described in numerous patents including U.S. Pat. Nos. 6,521,865 and 6,131,266. Such assemblies can readily be modified for use with an ultra-fast pulse laser. Generally, a laser beam source may be positioned to direct the beam from the laser beam source to remove material from a substrate held by a fixture. In some embodiments, a polymeric tube can be disposed in a rotatable collet fixture of a machine-controlled apparatus that positions the tubing relative to a laser. According to machine-encoded instructions, the tube can be rotated and moved axially relative to the laser which can also be machine-controlled. The laser selectively removes the material from the tubing resulting in a pattern cut into the tube. The tube is therefore cut into the discrete pattern of a finished stent.

In certain embodiments, the process of cutting a pattern for the stent into the tubing can be automated except for loading and unloading the length of tubing. The automation may be done, for example, using a CNC-opposing collet fixture for axial rotation of the length of tubing. A collet fixture may act in conjunction with a CNC X/Y table to move the length of tubing axially relative to a machine-controlled laser as described. The program for control of the apparatus is dependent on the particular configuration used and the pattern formed. CNC equipment manufactured and sold by Anorad Corporation in Hauppauge, N.Y. may be used for positioning the tube.

It is desirable for a stent to have a stent pattern which allows the strain experienced by the stent to be spread or distributed over a relatively large area rather than being highly concentrated when the stent is deformed. During crimping and expansion, curved regions configured to bend can experience a strain that is localized. Such regions of the stent can be the most susceptible to fracture.

Figure 9:
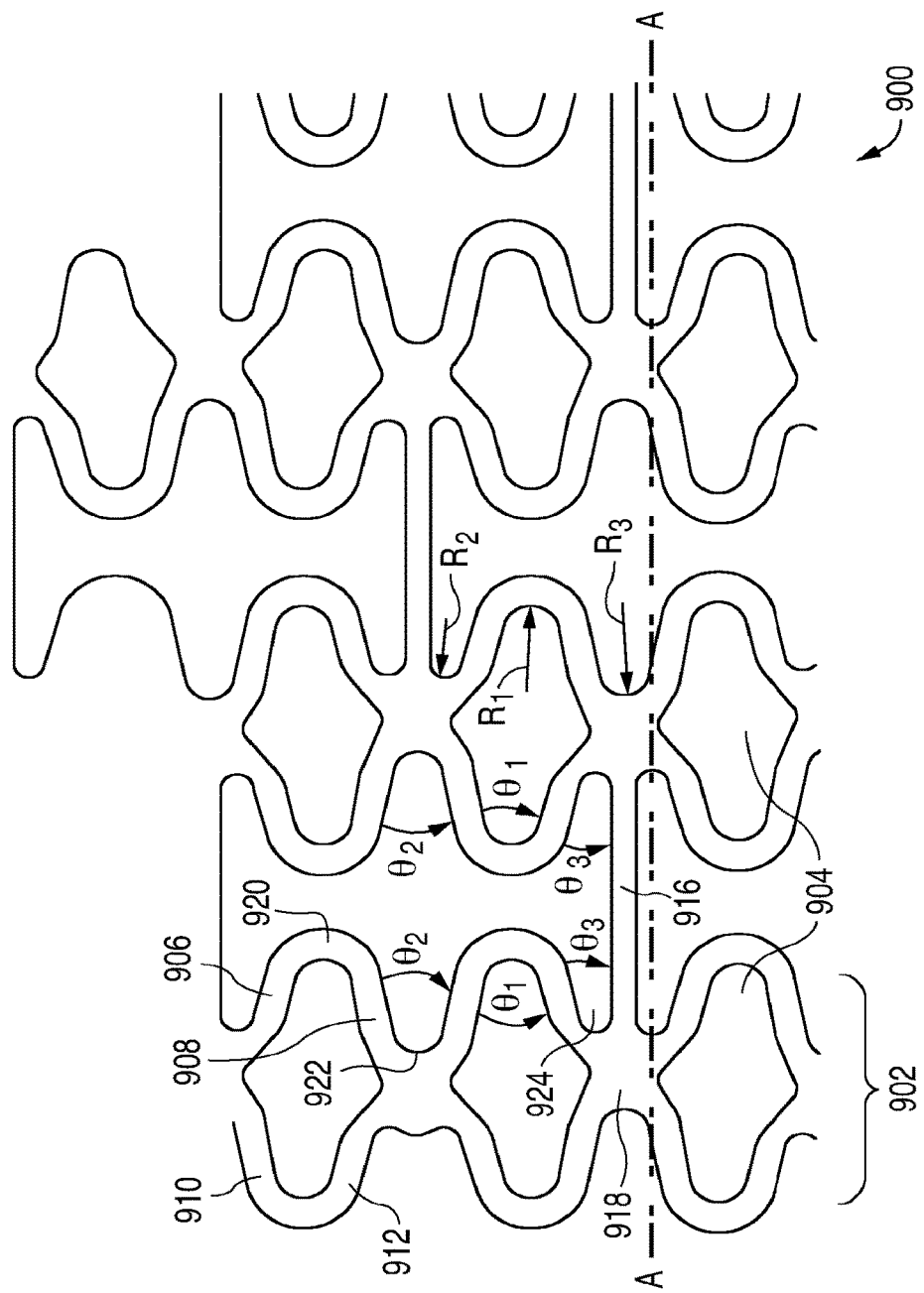
FIG. 9 depicts an exemplary stent pattern.

FIG. 9 depicts an exemplary stent pattern 900 for use with embodiments of a polymeric tube or a sheet. In an embodiment, stent pattern 900 can be cut from a polymeric tube using embodiments of the laser machining process described herein. The polymeric tube can be a radially and/or axially expanded tube, as described above.

Stent pattern 900 is shown in a flattened condition so that the pattern can be clearly viewed. When the flattened portion of stent pattern 900 is in a cylindrical form, it forms a radially expandable stent.

As depicted in FIG. 9, stent pattern 900 includes a plurality of cylindrical rings 902 with each ring including a plurality of diamond shaped cells 904. Embodiments of stent pattern 900 may have any number of rings 902 depending a desired length of a stent. For reference, line A-A represents the longitudinal axis of a stent using the pattern depicted in FIG. 9. Diamond shaped cells 904 are made up of bar arms 906 and 908 that form a curved element and bar arms 910 and 912 that form an opposing curved element.

Pattern 900 further includes linking arms 916 that connect adjacent cylindrical rings. Linking arms 916 are parallel to line A-A and connect adjacent rings between intersection 918 of cylindrically adjacent diamond-shaped elements 904 of one ring and intersection 918 of cylindrically adjacent diamond shaped elements 904 of an adjacent ring. As shown, linking elements connect every other intersection along the circumference.

Generally, a stent is allowed to be crimped or expanded through flexing of curved or bending elements. A stent with a pattern 900 can be crimped or compressed principally through flexing of curved elements between (1) bar arms within diamond-shaped cells symmetric about the longitudinal axis bar arms, for example, bar arms 906 and 908 with an angle $\theta_1$ (bending or curved element 1)

(2) bar arms of cylindrically adjacent diamond-shaped cells, for example, bar arms 906 and 908 with an angle $\theta_2$ (bending or curved element 2)

(3) a bar arm of a diamond-shaped cell and a linking bar arm 916, for example, bar arms 908 and linking bar arm 916 with an angle $\theta_3$ (bending or curved element 3)

When a stent having a stent pattern 900 is crimped, bending elements 1, 2, and 3 flex inward and angles $\theta_1$, $\theta_2$, and $\theta_3$ decrease, allowing the stent to be radially compressed. Similarly, a stent is allowed to expand when angles $\theta_1$, $\theta_2$, and $\theta_3$, increase. With respect to bending elements 1 and 2, each of the bar arms of the respective bending elements tend to bend toward or away from each other. However, in bending element 3, the bar arm of the diamond-shaped element tends to bend toward the linking bar arm, the linking bar arm which tends to remain relatively parallel to the longitudinal axis.

The region at and adjacent to the apices of the bending elements: apex 920, 922, and 924, experience a high degree of stress and strain during crimping and expansion. The spatial distribution of the strain depends on the geometry of the bending portion. The strain can vary from being highly localized to being widely distributed in the apex regions.

Figure 10A:
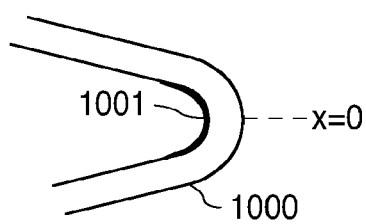
FIG. 10A depicts an exemplary bending element of a stent pattern.
Figure 10B:
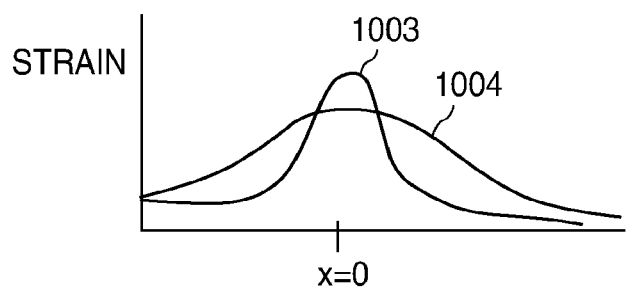
FIG. 10B depicts the strain distribution along a line offset from the neutral axis of the bending element depicted in FIG. 10B.

FIG. 10A depicts an exemplary bending element 1000 and FIG. 10B depicts the strain distribution along a line 1001 at the inner surface of bending element 1000 that follows its curvature. Curve 1003 corresponds to a strain distribution that is highly localized while curve 1004 represents a more disperse strain distribution. In general, a more disperse strain distribution is more desirable since the more localized the strain, the more likely is mechanical failure at the region of strain concentration. As shown by curve 103, the maximum strain experienced by bending arm 1000 increases the more concentrated the strain distribution, resulting in a higher likelihood of fracture.

In general, the radius of curvature of a bending arm is directly related to the distribution of stress in a bending arm that is in either a crimped or compressed state. The larger the radius of curvature of an unstressed bending arm, the more widely dispersed or distributed is the strain.

Therefore, the stress concentration in bending elements 1, 2, and 3 can be controlled at least by the radius of curvature, $R_1$, $R_2$, and $R_3$, respectively, which are depicted in FIG. 10. In general, the radii should be as large as possible while still allowing a stent to reach a desired crimped diameter.

An exemplary stent with a stent pattern 900 can have six diamond-shaped cells with a circumference of 0.264 in. In general, a stent with stent pattern 900 can have a ratio of its outer circumference to the number of cells around the circumferences of 0.264 in/6 cells or 0.044 in/cell. In some embodiments, a stent having a disperse strain distribution in curved elements can have $R_1$=0.0056 in, $R_2$=0.0034, and/or $R_3$=0.005. In other embodiments, such a stent can have an $R_1$ between 0.004 in and 0.006 in, $R_2$ between 0.0025 in and 0.004 in, and/or $R_3$ between 0.004 in and 0.006 in.

Embodiments of the stents above tend to have relatively disperse distribution of strain in the apex regions of bending elements 1, 2, and 3. For example, the magnitude of stress tends to be below the ultimate strength of stents fabricated according to the embodiments described herein.

As discussed above, prior to delivery into the body a stent is compressed or crimped onto a catheter so that it can be inserted into small vessels. Once the stent is delivered to the treatment site, it can be expanded or deployed at a treatment site. Generally, stent crimping is the act of affixing the stent to the delivery catheter or delivery balloon so that it remains affixed to the catheter or balloon until the physician desires to deliver the stent at a treatment site. There are numerous crimpers available for crimping stents including, but not limited to, the roll crimper, collet crimper, and wedge crimper.

Conventionally, crimping is performed at ambient conditions. A shortcoming of polymeric stents as compared with metallic stents is that they can be relatively brittle at ambient conditions. Such polymers have a Tg that is above ambient conditions. As discussed above, there are regions of a stent subjected to relatively high stress and strain during crimping. Thus, such regions are susceptible to mechanical failure in such high strain regions due to the brittle nature of the polymer at ambient conditions. Another shortcoming of polymeric stents with respect to crimping is that polymeric stents can have a tendency to recoil outward from a crimped diameter. The recoiling can result in poor stent retention.

Certain embodiments of a crimping method for polymeric stents are described herein which reduce or eliminate recoil and reduce or eliminate mechanical damage due to the crimping process. In some embodiments, a stent may be crimped at a temperature above ambient conditions that reduces or eliminates recoil and mechanical failure.

As discussed above, below Tg a polymer tends to be brittle and thus is susceptible to fracture at a relatively low elongation when subjected to stress. Generally, the glass transition temperature, Tg, is the temperature at which the amorphous domains of a polymer change from a brittle vitreous state to a solid deformable or ductile state at atmospheric pressure. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. The Tg of a given polymer can be dependent on the heating rate and can be influenced by the thermal history of the polymer. Furthermore, the chemical structure of the polymer heavily influences the glass transition by affecting mobility.

Figure 11:
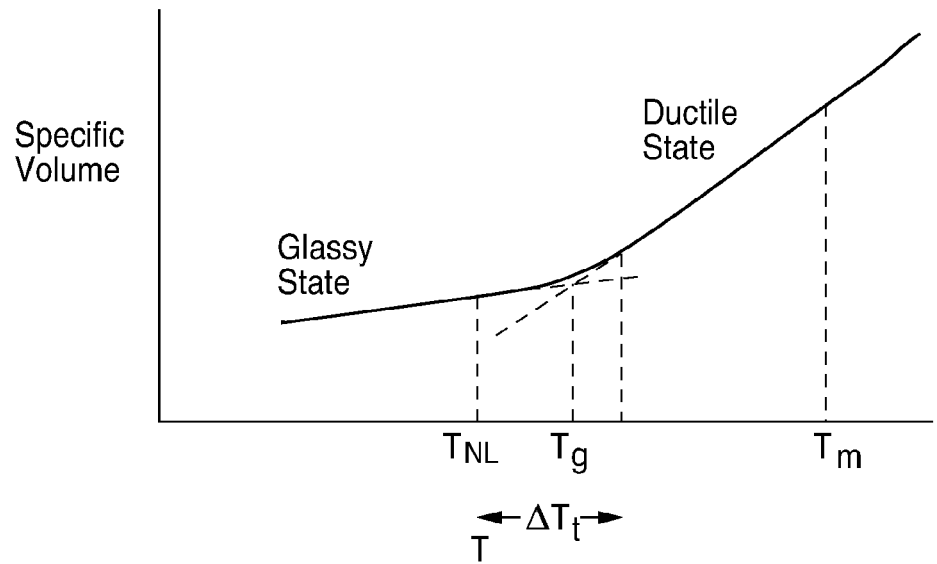
FIG. 11 is a schematic plot of the specific volume of an amorphous polymer vs. temperature.

The transition from the brittle to ductile state is not sharp or discontinuous for an amorphous polymer. Rather, as the temperature of the polymer approaches Tg, the polymer becomes less brittle. The smoothness of the transition for an amorphous polymer can be illustrated by the temperature dependence of a number of properties. For example, FIG. 11 is a schematic plot of the specific volume of an amorphous polymer vs. temperature. In the glassy and ductile states, the specific volume vs. temperature is substantially linear, with each state having a different slope. As FIG. 11 shows, as the temperature is increased in the linear glassy region, at a temperature $T_{NL}$ the slope becomes nonlinear through a continuous transition region $\Delta T_t$. As shown, the Tg is determined by the intersection of the slope of the specific volume vs. temperature in the brittle and ductile states.

The specific volume data depicted in FIG. 11 for an amorphous polymer can be obtained in a dilatometer. In this apparatus, a sample is placed in a glass bulb and a confining liquid, usually mercury, is introduced into the bulb so that the liquid surrounds the sample and extends partway up a narrow bore glass capillary tube. A capillary tube is used so that relatively small changes in polymer volume caused by changing the temperature produce easily measured changes in the height of the mercury in the capillary.

The determination of Tg for amorphous materials, such as polymers by dilatometric methods (as well as by other methods) are found to be rate dependent. For example, a higher cooling rate can result in a higher value of Tg. Tg can also be determined using differential scanning calorimetry. Other methods can also be used that use measurements of quantities such as density, dielectric constant, and elastic modulus.

The increase in the specific volume is associated with increased molecular motion which can result in less brittle behavior. Therefore, a polymer deformed in this region is less susceptible to mechanical failure. Additionally, a deformed polymer is less likely to recoil towards the undeformed state. This reduction in the polymers desire to return to an undeformed state is due to the large scale segmental chain motion that is possible for the polymer above Tg. This increased chain motion will result in very low residual stress in the deformed state, which reduces the desire for the polymer to return to an undeformed state. For polymers deformed below Tg, there will be some retained stress in the polymer, which will result in a desire for the polymer to return to the undeformed state. Therefore, it can be desirable for a stent to be at a temperature above the nonlinear transition, $T_{NL}$, during crimping. In some embodiments, a polymeric stent may be at a temperature between $T_{NL}$ and Tg, or more narrowly in a range $T_{NL}+0.90*\Delta T_t$, $T_{NL}+0.70*\Delta T_t$, $T_{NL}+0.50*\Delta T_t$, $T_{NL}+0.30*\Delta T_t$, or $T_{NL}+0.10*\Delta T_t$, during crimping.

In further embodiments, the stent may be crimped at a selected temperature Ts, which is less than Tg. Other embodiments include crimping in a temperature interval $Ts-\Delta T_s < T < Ts+\Delta T_s$. For example, Ts may be Tg−25° C. and $\Delta T_s$ may be 5° C., 15° C., or 20° C.

Furthermore, some embodiments may include a stent at a temperature at or above Tg during crimping. However, crimping at such a temperature should be done in a manner that reduces or prevents loss of induced orientation. The higher the molecular weight of the polymer and/or faster the crimping process the lower the loss of orientation.

A device for crimping the polymeric stent can resemble any crimping device as is known in the art. Additionally, the device can be especially modified so that it can heat the stent during crimping. In some embodiments, the device can apply pressure and heat simultaneously. In these or other embodiments, after crimping, the crimping device can hold the stent at an elevated temperature, which may be selected such that it is greater than, equal to, or less than the selected crimping temperature or may be selected to specifically exclude temperatures greater than, equal to, or less than the selected crimping temperature. In some embodiments, the device crimps the polymeric stent while the stent is heated by other means.

The stent can be heated for up to one hour, 30 seconds to one hour, or for 30 seconds. In some embodiments, the stent is heated long enough that the material becomes ductile enough to adequately lower the brittleness of the stent. Adequate means having a value for the parameter in question such that one of ordinary skill in the art would expect the invention to function in the particular application. For example, "adequately lower the brittleness of the stent" means that the brittleness of the stent is reduced enough to warrant the extra heating step and the extra cost and complication of the heating step, as viewed by one of ordinary skill in the art.

For the purposes of the present invention, the following terms and definitions apply:

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLES

Some embodiments of the present invention are illustrated by the following prophetic Examples. The Examples are being given by way of illustration only and not by way of limitation. The parameters and data are not be construed to unduly limit the scope of the embodiments of the invention.

Embodiments of a stent can be fabricated from poly(L-lactide) (PLLA).

Tube Manufacturing

A polymeric tube can be fabricated using a 1 in single screw extruder. The temperature of the polymer melt within the extruder can be between 370° F. and 470° F., 390° F. and 450° F., or more narrowly, between 310° F. and 430° F. The residence time in extruder can be less than 15 minutes, less than 10 minutes, or more narrowly, less than 5 minutes. The tube exiting the die can be cooled or quenched in a water bath. The length of the quench or cooling distance can be less than 2 inches, less than 1 inch, or more narrowly less than ¾ inch. The pull rate of the tube from the die can be less than 25 ft/min, 20 ft/min, or more narrowly less than 16 ft/min. The barrel pressure inside the extruder can be between 1800 and 2200 psi. The axial draw down ratio of the tube exiting the die can be approximately 3:1.

The pre-extrusion and post extrusion number average molecular weight (Mn), weight average molecular weight (Mw), and polydispersity (PD) can be as follows:

Pre-extrusion—Mn can be between 255 K and 275 K, Mw can be between 450 510 K and 530 K, and PD can be between 1.9 and 2

Post-extrusion—Mn can be between 170 K and 190 K, Mw can be between 370 K and 390 K, and PD can be between 2 and 2.1.

The post-extrusion % crystallinity can be between 10% and 15%.

The post-extrusion strain to failure (measured at 98.6° F. (37° C.) and a stretch rate of 0.5 inch/min) can be between 290% and 310%.

Radial Expansion

The extruded tubing can be expanded from 0.018 in inside diameter (ID)/0.056 in outside diameter (OD) to (0.065 in to 0.080 in ID)/(0.077 in to 0.092 in OD), with 30-60% longitudinal stretch of the tube. The tubing can be expanded by blow molding, as described above, into a glass mold. The degree of crystallinity after expansion can be between 35% and 55%. The temperature of tube during radial expansion can be between 160° F. and 180° F.

The pre-blow molding and post blow molding Mn, Mw, and PD can be as follows:
  Pre-blow molding—Mn can be between 175 K and 185 K, Mw can be between 375 K and 385 K, and PD can be between 2 and 2.1.
  Post-blow molding—Mn can be between 160 K and 170 K, Mw can be between 335 K and 345 K, and PD can be between 1.9 and 2.

Laser Machining

Laser machining can be performed with a laser having a 120 femto second pulse. The wavelength of the laser can be 800 nm. The pre-laser cutting and post laser cutting Mn, Mw, and PD can be as follows:
  Pre-laser cutting—Mn can be between 160 K and 170 K, Mw can be between 335 K and 345 K, and PD can between 1.9 and 2.
  Post laser cutting—Mn can be between 115 K and 125 K, Mw can be between 275 K and 285 K, and PD can between 2.25 and 2.35.

Stent Pattern

A stent pattern as depicted in FIG. 9 can be cut with the laser. Stent struts can have a rectangular or square cross-section. For example, the struts can measure 0.006×0.0065 in (150×150 micron).

Crimping

As indicated above, the stent can be crimped from the cut diameter to a desired diameter onto a support element, such as a balloon. A sliding wedge style crimper can be used. The crimp cycle may be between about 25 and 30 seconds. The stent can be heated to a temperature between 28° C. and 32° C. during crimping. The stent can be crimped from a 0.084 in OD to a 0.053 in OD.

Deployment

The crimped stent can be deployed with an outward radial pressure in the balloon of 7 atm to 0.118 (3.0 mm) ID or a pressure of 21 atm to 0.138 in (3.5 mm) ID.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent comprising:
  forming a polymer tube made of a biodegradable polymer, wherein forming the polymer tube comprises forming an extruded polymer tube and quenching the extruded polymer tube from a first temperature, the first temperature being above a melting temperature of the biodegradable polymer, to a second temperature, the second temperature being below a glass transition temperature of the biodegradable polymer, such that the biodegradable polymer of the formed tube is an amorphous or substantially amorphous glassy polymer;
  processing the tube to increase the crystallinity of the biodegradable polymer from amorphous or substantially amorphous to between 35% and 55%;
  cutting a pattern in the processed tube to form a cylindrically-shaped scaffold, wherein the scaffold includes a pattern of interconnecting struts,
  wherein the pattern comprises a plurality of cylindrical rings of struts and longitudinal linking struts connecting the rings,
  wherein the rings include bending elements including struts that flex inward to allow crimping of the scaffold and flex outward to allow expansion of the scaffold,
  wherein the scaffold is radially expandable in a blood vessel of a body and has adequate radial strength to hold open the blood vessel, and
  wherein the stent comprises the scaffold.

2. The method of claim 1, wherein the biodegradable polymer is a copolymer.

3. The method of claim 1, wherein the biodegradable polymer is a mixture of polymers.

4. The method of claim 1, wherein the processing comprises radial expansion of the tube to a target diameter at a third temperature, the third temperature being above the glass transition temperature (Tg) of the biodegradable polymer.

5. The method of claim 4, wherein a radial draw ratio of the radial expansion of the tube is between 2 and 6.

6. The method of claim 1, further comprising crimping the stent on to a balloon at a diameter less than a target diameter so that the stent can be delivered into the blood vessel.

7. The method of claim 1, wherein the processing comprises increasing a temperature of the tube above the glass transition temperature (Tg) of the biodegradable polymer.

* * * * *